United States Patent [19]

Mueller et al.

[11] Patent Number: 5,281,716
[45] Date of Patent: Jan. 25, 1994

[54] METHOD FOR PREPARING 7-OXABICYCLOHEPTYL SUBSTITUTED OXAZOLE AMIDE PROSTAGLANDIN ANALOG INTERMEDIATES USEFUL IN THE PREPARATION OF ANTI-THROMBOTIC AND ANTI-VASOSPASTIC COMPOUNDS

[75] Inventors: Richard H. Mueller, Ringoes; Janak Singh, Lawrenceville, both of N.J.

[73] Assignee: Bristol-Myers Squibb Company, Princeton, N.J.

[21] Appl. No.: 20,948

[22] Filed: Feb. 22, 1993

Related U.S. Application Data

[63] Continuation-in-part of Ser. No. 900,384, Jun. 18, 1992, abandoned.

[51] Int. Cl.$^5$ ............................................ C07D 493/08
[52] U.S. Cl. .................................. 548/236; 548/237
[58] Field of Search ........................................ 548/236

[56] References Cited

U.S. PATENT DOCUMENTS 5,100,889  3/1992  Misra et al. ..................... 548/236

FOREIGN PATENT DOCUMENTS 0476994  3/1992  European Pat. Off. .

OTHER PUBLICATIONS

Misra et al., "Thromboxane Receptor Antagonist BMS-180291: A New Pre-Clinical Lead," Bioorganic and Medicinal Chemistry, vol. 2, No. 1, pp. 73–76, 1992.

Primary Examiner—Donald G. Daus
Attorney, Agent, or Firm—Burton Rodney

[57] ABSTRACT

A method is provided for preparing oxazole intermediates of the structure

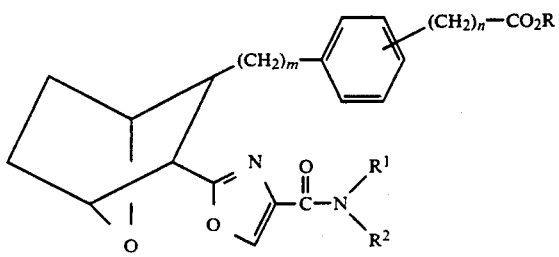

(wherein R is alkyl) wherein an oxazoline of the structure

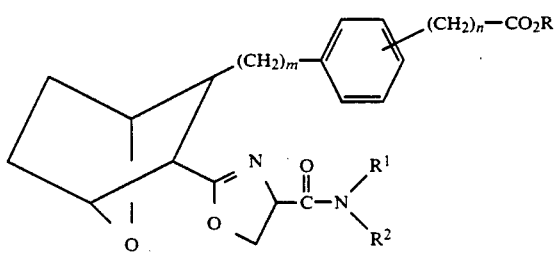

is oxidized employing an oxidizing agent such as cupric bromide, a base such as 1,8-diazabicyclo[5.4.0]undec-7-ene (DBU), and a non-hydride donor amine base such as hexamethylenetetraamine (HMTA). The resulting oxazole may be hydrolyzed to the final anti-thrombotic - anti-vasospastic compounds.

27 Claims, No Drawings

METHOD FOR PREPARING 7-OXABICYCLOHEPTYL SUBSTITUTED OXAZOLE AMIDE PROSTAGLANDIN ANALOG INTERMEDIATES USEFUL IN THE PREPARATION OF ANTI-THROMBOTIC AND ANTI-VASOSPASTIC COMPOUNDS

REFERENCE TO RELATED APPLICATIONS

This is a continuation-in-part of U.S. application Ser. No. 900,384, filed Jun. 18, 1992, now abandoned.

FIELD OF THE INVENTION

The present invention relates to a method for preparing a 7-oxabicycloheptyl substituted oxazole amide prostaglandin analog intermediate by oxidation of corresponding oxazoline compound employing an oxidizing agent such as cupric bromide, in combination with a base such as DBU, and a non-hydride donor amine base such as hexamethylenetetraamine (HMTA). The resulting oxazole may be hydrolyzed to a final anti-thrombotic—anti-vasospastic product.

BACKGROUND OF THE INVENTION

U.S. Pat. No. 5,100,889 to Misra et al discloses 7-oxabicycloheptyl substituted heterocyclic amide prostaglandin analogs which are thromboxane $A_2$ ($TXA_2$) receptor antagonists or combined thromboxane $A_2$ receptor antagonist/thromboxane synthetase inhibitors useful, for example, in the treatment of thrombotic and/or vasospastic diseases, and have good duration of action. Examples of compounds disclosed in Misra et al have the structural formula I

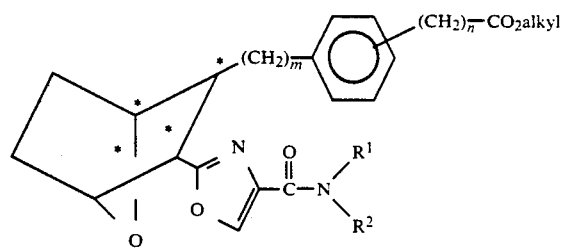

and including all stereoisomers thereof, wherein
m is 1, 2 or 3; n is 0, 1, 2, 3 or 4;
$R^1$ is hydrogen, lower alkyl, lower alkenyl, lower alkynyl, aralkyl, aryl, cycloalkyl, cycloalkylalkyl, or amide

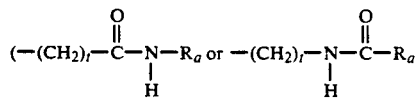

wherein
t is 1 to 12 and $R_a$ is lower alkyl, aryl, cycloalkyl, or cycloalkylalkyl);
$R^2$ is hydrogen, lower alkyl, aryl, or aralkyl; or $R^1$ and $R^2$ together with the nitrogen to which they are linked may form a 5- to 8- membered ring;
$R^3$ is lower alkyl, aryl or aralkyl; and
$R^{3a}$ is hydrogen, lower alkyl, aryl or aralkyl.

Misra et al disclose that these compounds may be prepared from the oxazoline XV'

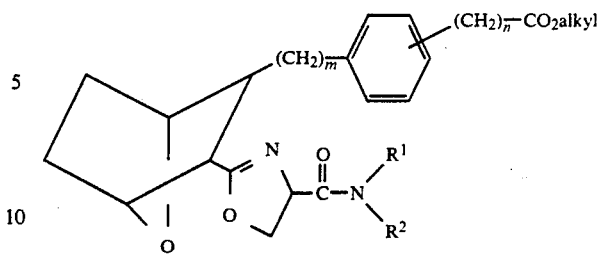

which is made to undergo oxidation using manganese dioxide, or nickel peroxide, or preferably cupric bromide and 1,8-diazabicyclo[5.4.0]undec-7-ene (DBU) to form the oxazole.

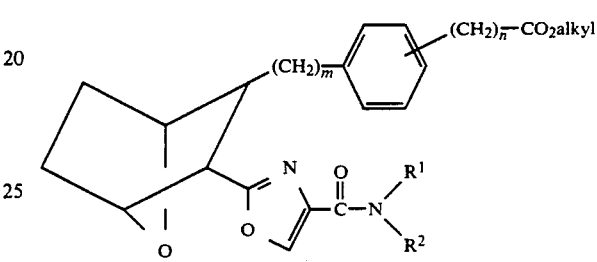

The cupric bromide oxidation is carried out at a temperature of within the range of from about 20° C. to about 70° C., employing a molar ratio of cupric bromide to XV' of within the range of from about 2:1 to about 6:1 and a molar ratio of cupric bromide to DBU of within the range of from about 1:1 to about 1:3 in an inert solvent such as ethyl acetate or preferably ethylacetate/chloroform (1:1, v/v).

The so-formed oxazole may then be hydrolyzed by treatment with an aqueous solution of alkali metal base and then aqueous acid to form the corresponding acid.

In accordance with the present invention, it has now been found that the above oxidation of the oxazoline to the oxazole can be dramatically improved in cost, speed, yield and reproducibility by employing with cupric bromide and DBU, a non-hydride donor amine, preferably hexamethylenetetraamine, in an inert organic solvent such as dichloromethane.

DESCRIPTION OF THE INVENTION

The method of the present invention includes the step of subjecting oxazoline XV'

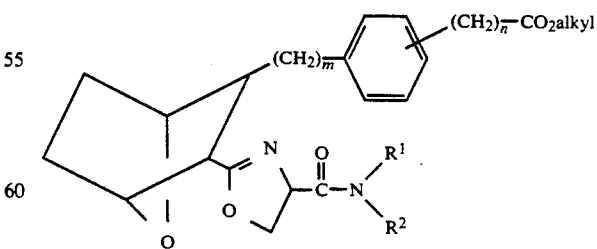

wherein m, n, $R^1$ and $R^2$ are as defined below (and as in the above-mentioned Misra et al patent), to oxidation using cupric bromide or ferric bromide, preferably cupric bromide, and a base which is 1,8-diazabicyclo[5.4.0]undec-7-ene (DBU) or 1,5-diazabicyclo[4.3.0]non- 5-ene (DBN), preferably DBU, in the presence of a non-hydride donor amine base, preferably hexamethylenetetraamine, to form the corresponding oxazole XVI'

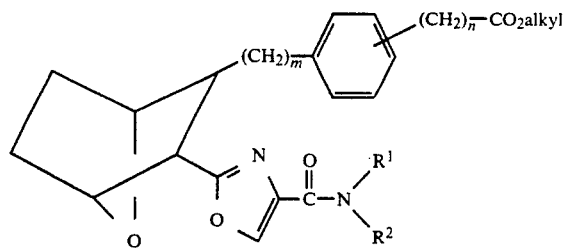

The above oxidation is carried out in the presence of an inert organic solvent such as dichloromethane.

The so-formed oxazole XVI may be hydrolyzed, for example, by treatment with an aqueous solution of alkali metal base (to form the corresponding salt) and then with aqueous acid (such as HCl) to form the corresponding acid.

In the above formulae XV' and XVI' compounds
n is 0, 1, 2, 3 or 4;
m is 1, 2 or 3;
$R^1$ is hydrogen, lower alkyl, aryl, aralkyl, cycloalkyl, cycloalkylalkyl or an amide

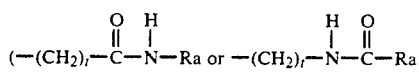

wherein
t is 1 to 12 and Ra is lower alkyl, aryl, cycloalkyl or cycloalkylalkyl);
$R^2$ is hydrogen, lower alkyl, aryl, or aralkyl; or
$R^1$ and $R^2$ together with the N to which they are linked form a 5- to 8-membered ring which contains only the single N heteroatom.

The term "non-hydride donor amine base" as employed herein refers to an amine that does not have an αH or does not lose H easily at alpha carbon and therefore can withstand the oxidation step described herein without losing H. The non-hydride donor amine bases which are suitable for use herein include amines which do not have an α-hydrogen (such as H* in the structure shown below

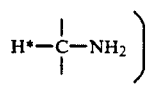

or amines which have an α-H which is not readily removable under oxidation conditions, such as monocyclic, bicyclic or tricyclic amines. Examples of such amine bases which do not have an α-H include (alkyl)-cycloalkyl amines such as prepared by the Ritter reaction ("Organic Reactions," Vol. 17, edited by W. G. Dauben et al, Chapter 3, "The Ritter Reaction" Krimen et al (1969) p. 216 et seq.), for example

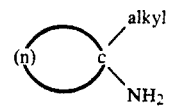

wherein n is 1, 2 or 3 carbons, such as

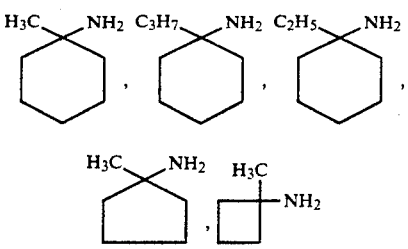

as well as (aryl)cycloalkyl amines such as

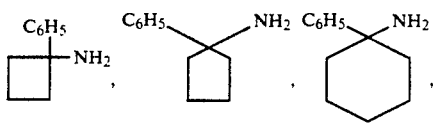

bicycloalkyl amines such as

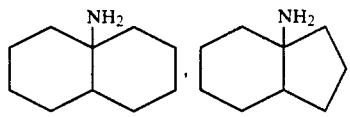

In addition, the non-hydride donor amines suitable for use herein include tetraalkyl cyclicamines

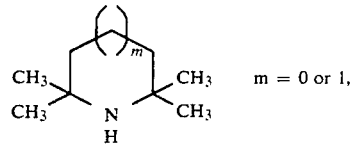   m = 0 or 1, tricyclic amines such as 1-adamantanamine

("The chemistry of the amine group," Edited by S. Patai, (Interscience, (1968), p. 46); as well as tertiary carbinamines prepared by the Hofmann reaction (Organic Reactions Vol. III, Edited by R. Adams et al, Chapter 7, "The Hofmann Reaction" Wallis et al, or by the Ritter reaction, p. 268 et seq.)

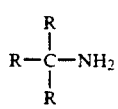

wherein R is $C_1$–$C_5$ alkyl or aryl.

Tricyclic amines which do have an α hydrogen, but are not susceptible to easy oxidation include hexamethylenetetraamine (HMTA), diazobicyclooctane (DABCO), quinuclidine, or 1-azaadamantane

Examples of preferred non-hydride donor amine bases suitable for use herein include hexamethylenetetraamine (HMTA), tert-butylamine, diazabicyclooctane (DABCO) or quinuclidine, most preferably hexamethylenetetraamine.

In carrying out the method of the invention, the oxidation is carried out at a temperature within the range of from about 20° C. to 70° C., preferably from about 10° to about 25° C., preferably under an inert atmosphere such as argon or nitrogen.

The method of the invention may be carried out in a single charge or double charge, the single charge method being preferred.

In the single charge method, each of the metal bromide, base such as DBU and non-hydride donor amine base are completely charged in a single addition. In this method, the metal bromide is employed in a molar ratio to oxazoline XV' of within the range of from about 2.5:1 to about 5:1, preferably from about 3:1 to about 4:1, and most preferably about 4:1; the base is employed in a molar ratio to oxazoline of within the range of from about 2.5:1 to about 5:1, preferably from about 3:1 to about 4:1, and most preferably about 4:1; and the non-hydride donor amine base is employed in a molar ratio to oxazoline of within the range of from about 2.5:1 to about 5:1, preferably from about 3:1 to about 4:1, and most preferably about 4:1. In a most preferred method hexamethylenetetraamine is employed as the non-hydride donor amine and each of cupric bromide, DBU and hexamethylenetetraamine (HMTA) will be employed in an amount to provide about 4 molar equivalents of each to each molar equivalent of oxazoline.

The above reaction will be carried out for a period of from about 4 to about 24 hours, preferably from about 4 to about 6 hours, which is substantially less than required in cupric bromide-DBU oxidations in the absence of HMTA. Further, in the method of the invention, the reaction is complete after a single charge, whereas in prior art methods three or more charges of reagents are required to complete the reaction.

In the double charge method, each of the metal bromide, base such as DBU and non-hydride donor amine base will be divided into two charges. Each of the first charges will be employed in amounts so as to provide a molar ratio of metal bromide to oxazoline XV' of within the range of from about 1.5:1 to about 2.5:1, preferably about 2:1, a molar ratio of base such as DBU to oxazoline of within the range of from about 1.5:1 to about 2.5:1, preferably about 2:1, and a molar ratio of non-hydride donor amine to oxazoline within the range of from about 1.5:1 to about 2.5:1, preferably from 2:1.

The reaction of the oxazoline with the initial charge will be for a period within the range of from about 3 to about 10 hours, preferably from about 5 to about 7 hours.

Thereafter, a second charge of each of the metal bromide, base and non-hydride donor amine in amounts approximately the same as in the first charge will be added to the reaction mixture and the reaction will be continued for a period of within the range of from about 10 to about 20 hours, preferably from about 8 to about 15 hours.

The total reaction time required will be substantially less than required in prior art cupric bromide-DBU oxidations. Further, in the method of the invention, the reaction is complete after two charges, whereas in prior art methods three or more charges of reagents are required to complete the reaction.

In each of the above methods, the preferred oxidizing agent is cupric bromide, the preferred base is DBU and the preferred non-hydride donor amine is hexamethylenetetraamine.

The term "lower alkyl" or "alkyl" as employed herein includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents, an aryl substituent, an alkyl-aryl substituent, a haloaryl substituent, a cycloalkyl substituent, or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, and/or alkoxy groups.

The term "aryl" or "Ar" as employed herein refers to monocyclic or bicyclic aromatic groups containing from 6 to 10 carbons in the ring portion, such as phenyl or naphthyl. Aryl (or Ar), phenyl or naphthyl may include substituted aryl, substituted phenyl or substituted naphthyl, which may include 1 or 2 substituents on either the phenyl or naphthyl such as lower alkyl, halogen (Cl, Br, I or F), alkylsulfonyl, and/or arylsulfonyl.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The compounds prepared by the method of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds prepared by the method of the invention, namely, cis-exo, cis-endo and all trans forms and stereoisomeric pairs may be prepared by employing starting materials and following the procedures as outlined in U.S. Pat. No. 4,143,054 and are fully disclosed in U.S. Pat. No. 5,100,889 which is incorporated herein by reference.

The nucleus in each of the compounds prepared by the method of the invention is depicted as

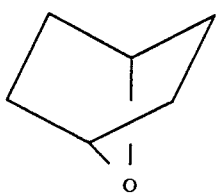

for matter of convenience; it will also be appreciated that the nucleus in the compounds of the invention may be depicted as

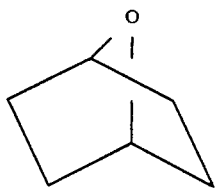

The compounds prepared by the method of this invention are thromboxane receptor antagonists and as such are useful as inhibitors of thromboxane receptor mediated actions. The term "thromboxane receptor antagonist" includes compounds which are so-called thromboxane $A^2$ receptor antagonists, thromboxane $A^2$ antagonists, thromboxane $A^2$/prostaglandin endoperoxide antagonists, TP-receptor antagonists, or thromboxane antagonists.

The compounds prepared by the method of the invention are also thromboxane synthetase inhibitors and thus are useful as inhibitors of thromboxane production.

Examples of various utilities of the compounds prepared by the method of the invention are set out in U.S. Pat. No. 5,100,889.

The following Examples represent preferred embodiments of the present invention. Unless otherwise indicated, all temperatures are expressed in degrees Centigrade.

EXAMPLE 1

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid, methyl ester

A. N-Pentyl-L-serinamide 1:1 oxalate salt

A(1). N-Pentyl-N2-[(phenylmethoxy)carbonyl]-L-serinamide

- A 5-L, 3-necked flask was charged with N-CBZ-L-serine (110 g, 0.46 mole) (CBZ=carbobenzyloxy) followed by dichloromethane (2.1 L). The resulting slurry was stirred under argon and treated with triethylamine (61.7 mL, 0.443 mole) over several minutes. The resulting hazy solution was cooled to an internal temperature of −35° and treated over 10 min with trimethylacetylchloride (51.06 mL, 0.415 mole) such that the internal temperature did not rise above −30°. The reaction was stirred an additional 40 min at −25° to −30°, treated with pyridine (35.2 mL, 0.435 mole) over 5 min and stirred an additional 10 min. Amylamine (51 mL, 0.44 mole) was added over 10 min while maintaining the internal temperature at −25° to −29°. The reaction was stirred for 30 min while warming to −25°. A precipitate formed during this warming. The reaction was further warmed to −10° over 40 min during which time the precipitate redissolved. After stirring an additional 20 min at −10°, the reaction was quenched by the addition of 500 mL of 1N HCl. The biphasic mixture was stirred for 20 min and transferred to a separatory funnel. The aqueous layer was extracted with dichloromethane (2×75 mL). The combined dichloromethane solutions were concentrated in vacuo to a weight of 500 g. Ethyl acetate (EtOAc) (2.25 L) was added and the organic solution was washed with 1N HCl (2×400 mL) and 1N K2CO3 (1×700 mL and 2×500 mL). The organic solution was dried (magnesium sulfate), filtered and concentrated in vacuo to the title compound which was used in the next step without purification.

A(2). N-Pentyl-L-serinamide. 1:1 oxalate salt

The part A(1) compound was evaporated from 95% ethanol (EtOH) to remove residual solvents. The residue was dissolved in 95% EtOH (1.28 L) and treated under nitrogen with 20% Pd(OH)2 (12.8 g). The mixture was stirred and sparged with hydrogen. After 2.5 h the catalyst was filtered off and washed with 95% EtOH. The filtrate was concentrated in vacuo to 73.1 g. A portion of this material (36.3 g, 0.21 mole) was redissolved in 95% EtOH (221 mL) and added slowly to a stirred room temperature solution of oxalic acid dihydrate (31.5 g, 0.25 mole) in 95% EtOH (221 mL). After the addition the resulting slurry was further diluted with 120 mL of 95% EtOH, stirred an additional 30 min and then heated to reflux. The slurry was treated with water (29 mL) to afford a clear, light yellow solution. After stirring an additional 40 min the heat was removed and the solution cooled. The resulting slurry was stirred at ambient temperature for 18 h, filtered and washed with 95% EtOH (1×72 mL, and 1×48 mL) and hexane (2×48 mL). Drying in vacuo produced 42.9 g (77.3%) of the title compound, mp 174° C.

B. {1S-[1α, 2α,3α,(R*),4α]}-2-{[3-({[1-(Hydroxymethyl)-2-oxo-2-(pentylamino)ethyl]amino}carbonyl)-7-oxabicyclo[2.2.1]hept-2-yl]-methyl}benzenepropanoic acid, methyl ester A solution of [1S-(1α,2α,3α,4α)]-2-[(3-carboxy-7-oxabicyclo[2.2.1]hept-2-yl)methyl]benzenepropanoic acid, methyl ester [prepared as described in Example 1 Part K of U.S. Pat. No. 5,100,889, (30.27 g, 95.06 mmol)]and dimethylformamide (DMF) (1.5 mL, 19.37 mmol) in CH2Cl2 (200 mL) was cooled to an internal temperature of 0 ° C. under an argon atmosphere. To the above solution was added oxalyl chloride (9.1 mL, 104.57 mmol) over ~2.5 minutes. After 2 hours, gas evolution had ceased. Toluene (30 mL) was added to the reaction mixture. The crude acid chloride solution was partially concentrated to an oil/solid mixture (43.37 g).

In a separate flask, a suspension of the Part A(2) compound (30.26 g, 114.50 mmol) in CH2Cl2 (200 mL) was treated sequentially, under argon, with DBU (33.4 mL, 223.28 mmol) and triethylamine (Et3N) (16.0 mL, 114.50 mmol). The resulting solution was cooled to −78 ° C. The crude acid chloride was redissolved in CH2Cl2 (350 mL), cooled to 8 ° C. under argon, and added to the solution of the amine via cannula such that the reaction temperature never exceeded −72 ° C. The addition process required 35 minutes. The flask containing the acid chloride solution was rinsed with CH2Cl2 (30 mL) which was transferred to the reaction mixture.

After 45 minutes the dry ice/acetone bath was removed and with vigorous stirring 1 N HCl (500 mL) was immediately added. The internal temperature quickly rose to −10 °C. After transferring to a separatory funnel, additional water (1 L) and $CH_2Cl_2$ (250 mL) were added. The layers were mixed and split. The aqueous layer was extracted with $CH_2Cl_2$ (250 mL). The organic phases were combined and washed with 1 N HCl (250 mL) and sat aq $NaHCO_3$ (500 mL). The aq $NaHCO_3$ solution was back-extracted with $CH_2Cl_2$ (250 mL). The organic solutions were combined, washed again with sat aq $NaHCO_3$ (250 mL) and sat aq NaCl (500 mL), dried ($MgSO_4$), filtered, concentrated, and left under high vacuum for 12 hours to give the crude title product (44.27 g).

A portion of this material (38.27 g) was placed in a flask with water (7.25 mL) and EtOAc (344 mL) and the mixture was brought to a boil. The resulting clear yellow solution was allowed to cool to room temperature and stand for 22 hours. EtOAc (125 mL) was added to slurry the all-engulfing white solid and the crystals were recovered via filtration. The white crystals were washed sequentially with EtOAc (2×75 mL) and hexanes (1×200 mL), air-dried (1.5 hours), and placed under high vacuum for 24 hours to give the title compound (33.87 g). Crystallization of all the crude material would have produced 39.17 g (87% crystallized yield) by extrapolation.

C.

[1S-(1α,2α,3α,4α)]-2-[[3-[4-[(Pentylamino)carbonyl]-4,5-dihydro-2-oxazolyl]-7-oxabicyclo[2.2.1]hept-2-yl]methyl]benzenepropanoic acid, methyl ester A solution of the Part B compound (25 g, 52.74 mmole) in dichloromethane (375 mL) was treated with magnesium sulfate (12 g) and stirred for 1 h. The drying agent was filtered and the filtrate was concentrated in vacuo. The solid residue was redissolved in dichloromethane (425 mL), cooled to an internal temperature of −5° and treated with triethylamine (11.03 mL, 79.11 mmole). Methanesulfonyl chloride (4.9 mL, 63.29 mmole) was added over 15 min while maintaining the internal temperature at −5° to 0°. The mixture was stirred for an additional 50 min and quenched with 1N HCl. The mixture was warmed to 20° and transferred to a separatory funnel. The acidic layer was extracted with additional dichloromethane (2×50 mL) and the combined organic extracts were washed with 1N HCl (2 ×130 mL), saturated sodium bicarbonate solution (2×150 mL) and brine (1×150 mL). The product rich organic solution was filtered and partially concentrated in vacuo to a weight of 360 g. After standing for several minutes at room temperature a gel developed. Additional dichloromethane was added (total solvent volume=500 mL) followed by triethylamine (8.8 mL). The resulting mixture was stirred at room temperature overnight. The solvent was evaporated and the oily residue was diluted with ethyl acetate (550 mL). The resulting solution was washed with water (3×120 mL). Each aqueous wash was treated with brine (15 mL) and back-extracted with fresh ethyl acetate (30 mL). The combined organic layers were washed with brine (1×150 mL), dried over sodium sulfate, filtered and concentrated in vacuo at <30°. The residue was dissolved in 90 mL of ethyl acetate. The resulting solution was concentrated to a volume of 62 mL and diluted with hexane (420 mL) to initiate crystallization. The resulting crystal mass was aged at room temperature for 7 h and placed in a refrigerator overnight. The product was filtered and washed with 10% ethyl acetate-hexane followed by hexane. Drying in vacuo produced 18.622 g (77%) of the title compound, mp 92° to 93° C.

D.

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid, methyl ester

| Two Charge Method |   |   |   |
|---|---|---|---|
| ($CuBr_2$/HMTA/DBU; second charge after 7 hours) | | | |
| 1st charge | $CuBr_2$ | /HMTA | /DBU |
| molar equiv. | 2 | 2 | 2 |
| 2nd charge | | | |
| molar eqiv. | 2 | 2 | 2 |

All glass apparatus was dried in a 125° oven overnight and assembled under Ar. $CH_2Cl_2$ was dried over 4A molecular sieves over night and sparged with Ar for 2 hours. The DBU was dried over 4A molecular sieves overnight and sparged with Ar for 30 minutes.

The $CuBr_2$ (4.46 g, 20.0 mM) was weighed out in a stoppered vial under a nitrogen curtain and added under a stream of Ar to a 250 mL 3-necked flask equipped with an Ar inlet and mechanical stirring. $CH_2Cl_2$ (60 mL) was added by pipette and hexamethylenetetraamine (HMTA) (2.8 g, 20.0 mM) was weighed out under $N_2$ and added to the stirred mixture. A brown mixture was formed with most of the $CuBr_2$ not dissolving. DBU (3.0 mL, 20.0 mM) was added dropwise to the stirred mixture. A black solution was formed. Part C oxazoline (4.57 g, 10.0 mM) was washed into the reaction mixture with 10 mL $CH_2Cl_2$; after 10 minutes a voluminous precipitate formed.

After 7 hours CuBr2 (4.46 g, 20.0 mM), HMTA (2.80 g, 20.0 mM), and DBU (3.0 mL, 20.0 mM) were added as above. The mixture was stirred overnight (24 hours). TLC (silica gel, ethyl acetate (EtOAc), $R_f$ SM 0.23, product $R_f$ 0.56 visualized by UV and CeriC ammonium molybdate) showed almost complete disappearance of SM (starting oxazoline).

The $CH_2Cl_2$ was evaporated on the rotary evaporator. Saturated $NH_4Cl$/conc. $NH_4OH$ (3:1, 50 mL) and EtOAc (50 mL) were added to the residue. The layers were separated and the aqueous layer washed with saturated $NH_4Cl$/conc. $NH_4OH$ (3:1, 2×25 mL), 10% citric acid (3×25 mL), 5% $NaHCO_3$ (25 mL), brine (25 mL), dried ($MgSO_4$ with stirring for 10 minutes), charcoaled (1 g with stirring for 30 minutes), filtered through Celite, and evaporated to give 4.44 g (97%); HPLC HI (215 nm) 95%, Part C compound, corresponding 5-bromo-oxazole 1.80%.

EXAMPLE 2

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoi acid, methyl ester

A.

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid, methyl ester

A(I)

Single Charge Method—I [single charge CuBr2/HMTA/DBU (3 mol. equiv. each)]

All glass apparatus was dried in a 125° overnight and assembled under Ar. The $CH_2Cl_2$ was dried over 4A molecular sieves overnight and sparged with Ar for 30 minutes.

The $CuBr_2$ (6.69 g, 30.0 mM) was weighed out in a stoppered vial under a nitrogen curtain and added under a stream of Ar to a 250 mL 3-necked flask equipped with an Ar inlet and mechanical stirring. $CH_2Cl_2$ (60 mL) was added by pipette and hexamethylenetetraamine (4.2 g, 30.0 mM) was weighed out under $N_2$ and added to the stirred mixture. A brown solution was formed with most of the $CuBr_2$ not dissolving. DBU (4.48 mL, 30.0 mM) was added dropwise to the stirred mixture. A black solution was formed. Example 1 Part C oxazoline (4.57 g, 10.0 mM) was washed into the reaction mixture with 10 mL $CH_2Cl_2$; after 10 minutes a voluminous precipitate formed. The mixture was stirred overnight (24 hours). TLC (silica gel, EtOAc, $R_f$ SM 0.23, product $R_f$ 0.56 visualized by UV and ceric ammonium molybdate) showed almost complete disappearance of SM.

A small amount of the precipitate was filtered from the reaction mixture and washed with $CH_2Cl_2$. It was identified as $(HMTA.HBr)_2CuBr$ complex. The $CH_2Cl_2$ was evaporated on the rotary evaporator. Saturated $NH_4Cl$/conc. $NH_4OH$ (3:1, 50 mL) and EtOAc (50 mL) were added to the residue. The layers were separated and the aqueous layer washed with EtOAc (3×50 mL). The combined EtOAc layers were washed with saturated $NH_4Cl$/conc. $NH_4OH$ (3:1, 2×25 mL), 10% citric acid (3×25 mL), 5% $NaHCO_3$ (25 mL), brine (25 mL), dried ($MgSO_4$ with stirring for 10 minutes), charcoaled (1 g with stirring for 30 minutes), filtered through Celite, and evaporated: 4.44 g (97%), HPLC HI 91.5%, starting oxazoline compound (SM) 0.045%, corresponding 5-bromo-oxazole 2.18%.

A(II)

Single Charge Method—II [single charge $CuBr_2$/HMTA/DBU (4 mol. equiv. each)]

HMTA (2.8 g, 5 mmol) was added to a mechanically stirred suspension of $CuBr_2$ (4.46 g, 20 mmol) in 30 mL deoxygenated dry $CH_2Cl_2$. DBU (3.13 mL, 20 mmol) was added to the brown mixture and the resulting warm dark brown solution was cooled in a water-bath for 5 minutes. Solid oxazoline (prepared in Example 1 Part C) (2.28 g, 5 mmol) was added and the mixture was stirred at room temperature. After 5 hours TLC (silica gel, EtOAc/Isopropanol 9:1, $R_f$ oxazole 0.65 and oxazoline 0.48, visualized by UV and ceric sulphate/ammonium molybdate) showed complete disappearance of the oxazoline starting material. The $CH_2Cl_2$ was evaporated on the rotary evaporator. Saturated $NH_4Cl$/conc. $NH_4OH$ (1:1, 40 mL) and EtOAc (40 mL) were added to the residue. The layers were separated and the aqueous layer extracted with EtOAc (3×10 mL). The combined EtOAc layers were washed with saturated $NH_4Cl$/conc. $NH_4OH$ (1:1, 3×10 mL). The aqueous washes were back extracted with 15 mL EtOAc. The combined organic extracts were washed with 10% citric acid (4×10 mL). These aqueous washes were extracted with 10 mL EtOAc. Combined organic extracts were further washed with brine (15 mL), 5% aqueous $NaHCO_3$ (10 mL) and brine (15 mL). The solution was dried ($MgSO_4$), stirred with charcoal (Darco 2 g) for 30 minutes and filtered through a pad of $MgSO_4$. The filtrate was evaporated to give 2.11 g (93% crude yield) of title ester. The product was purified by column chromatography over 200 mL K-60 silica gel using 2.5 liter EtOAc/hexane (1:2) for elution to give 1.86 g oxazole ester (yield 82%), mp 138°–39°, $[\alpha]_D = +14.3°$ (c=1, $CHCl_3$).

Analysis calc'd for $C_{26}H_{34}N_2O_5$ (MW 454.57): C, 68.70; H, 7.54; N, 6.16; $H_2O$, 0.0. Found: C, 68.61; H, 7.46; N, 6.36; H20, 0.0 (KF via desorption at 140° C.).

In both Example 1 Part D (two charge method) and Example 2 Part A(I) (single charge method-I), reactions were complete in ~24 hours with minimal unreacted starting oxazoline material (Example 1 Part D vs. Example 2 Part A(I) 0.0% oxazoline vs. 0.04% oxazoline by HPLC). In Example 2 Part A(II) (single charge method-II) reaction was complete in only 5 hours and contained a trace of oxazoline starting material, 0.02% by HPLC.

EXAMPLE 3

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid 1.0 N NaOH (8.92 mL, 8.92 mM) was added to the Example 1 ester (1.5 g, 3.30 mM) dissolved in THF (18 mL). The mixture was stirred rapidly for 3 hours. TLC (silica gel, EtOAc, $R_f$ Example 1 ester 0.58, $R_f$ title compound 0.2 visualized by UV and ceric ammonium molybdate/heat) shows no oxazoline starting material. The THF was evaporated; the aqueous residue was diluted to 25 mL with water and washed with 50 mL EtOAc. The EtOAc layer was backwashed with 5 mL water. The combined aqueous layers were acidified with 1 N HCl (10 mL) to pH 1 and extracted with EtOAc (3×75 mL). The combined EtOAc layers were washed with water (25 mL), brine (25 mL), dried ($MgSO_4$), and evaporated to give 1.42 g (98% crude yield) of title compound, HPLC HI (215 nm) 99.7.

The residue was dissolved in 15 mL hot $CH_3CN$, let stand for 3 hours at room temperature and at 0° for 3 hours. The crystals were filtered, washed with cold heptane, and dried under vacuum ON to give 1.28 g (88%) of the title compound, mp 150°–1° (darkens at 143°), HPLC HI (215 nm) 99.6.

Calc'd for $C_{25}H_{32}N_2O_5$ (440.54) C, 68.16; H, 7.32; N, 6.36. Found: C, 68.31; H, 7.35; N, 6.38.

EXAMPLE 4

[1S-(1α,2α,3β,4α)]-2-[[3-[4-[(Pentylamino)carbonyl]-2-oxazolyl]-7-oxabicyclo[2.2.1]hept-2-yl]methyl]benzenepropanoic acid, methyl ester

A.

[1S-[1α,2α,3β(R*),4α]]-2-[[3-[4,5-Dihydro-4-[(pentylamino)carbonyl]-2-oxazolyl]-7-oxabicyclo[2.2.1]hept-2-yl]methyl]benzenepropanoic acid, methyl ester Thermal Isomerization of cis-Oxazoline to trans-Oxazoline A solution of Example 1 Part C oxazoline (4.75 g, 10 mmol) in 40 mL xylenes (boiling range 137°–144° C.) was heated to 135° under argon. After 12 hours the reaction mixture was cooled to room temperature and treated with charcoal (~1 g Darco) with stirring for 20 minutes. The mixture was filtered through a pad of $MgSO_4$ and the solvent was evaporated. The residue was chromatographed over silica gel (K-60, 400 mL in a column with 25 mm diameter). The product was successively eluted with 50 mL hexane, 2L 25% EtOAc in hexane, 4L 50% EtOAc in hexane and 1L EtOAc, collecting 30 mL fractions. TLC-homogeneous fractions (92-202) were combined and evaporated to give 3.72 g (yield 82%) of title trans-oxazoline as a viscous liquid.

$[\alpha]_D = +22.5°$ (c=1, CHCl$_3$).

Anal. Calc'd for C$_{26}$H$_{36}$N$_2$O$_5$.0.09 H$_2$O.0.1 C$_6$H$_{12}$ (MW 456.58/466.82): C, 68.44: H, 8.11: N, 6.00: H$_2$O, 0.35. Found: C, 68.60; H, 8.48; N, 5.99; H$_2$O, 0.34 (via dissolution KF).

B.

[1S-(1α,2α,3β,4α)]-2-[[3-[4-(Pentylamino)carbonyl]-2-oxazolyl]-7-oxabicyclo[2.2.1]hept-2-yl]methyl]benzenepropanoic acid, methyl ester Hexamethylenetetraamine (HMTA, 3.22 g, 23 mmol) was added to a mechanically stirred suspension of CuBr$_2$ (5.13 g, 23 mmol) in 40 mL dry CH$_2$Cl$_2$. DBU (3.44 mL, 23 mmol) was injected to obtain a dark brown viscous solution. A gentle exotherm was observed during addition of DBU. The reaction mixture was cooled in a water bath to ambient temperature. A solution of Part A trans-oxazoline (3.48 g, 7.6 mmol) in 7 mL CH$_2$Cl$_2$ was added and the mixture was stirred under argon at room temperature. TLC after 30 minutes showed ~50% title product. A solid crystallized out during this reaction. After 5 hours, TLC still showed about 5% Part A starting material and a spot of higher R$_f$ than the title product. After 20 hours, the solid was filtered off and the filtrate was evaporated to obtain a dark brown oil. EtOAc (50 mL) and a mixture of aqueous NH$_4$OH and saturated aqueous NH$_4$Cl (1:1, 50 mL, pH 10) were added and the biphasic mixture was transferred to a separatory funnel. The blue aqueous layer was extracted with EtOAc (2×30 mL) and combined organic extracts were washed with a mixture of aqueous NH$_4$Cl and NH$_4$OH (1:1, 3×50 mL) and 10% citric acid (3×50 mL). The aqueous washes were combined and back extracted with 20 mL EtOAc. The organic extract was washed further with 30 mL brine, 30 mL aqueous NaHCO$_3$ and 30 mL brine. The organic layer was dried (MgSO$_4$) and then stirred with activated charcoal (Darco) for 0.5 hour. The mixture was filtered through a pad of MgSO$_4$ and the filtrate was evaporated to give a viscous liquid. The product was dried under vacuum for 2 hours to give 3.1 g (yield 85%, corrected for 0.25 mL EtOAc) of title compound. The product (3.09 g) was treated with 20 mL hexane and 5 mL acetone to give a solid. The solvent was removed completely and the solid was redissolved in 15 mL acetone. The solution was evaporated on a rotary evaporator to ~10 mL volume. A copious crystalline solid separated during concentration. The mixture was let stand at room temperature for 2 hours. The solid was filtered, washed with hexane and dried under vacuum to furnish 1.96 g (yield 54%) of title compound, mp ~43° C. A second crop of title compound was obtained from the mother liquor of the first crop: 0.37 g (yield 10%).

Anal. Calc'd for C$_{26}$H$_{34}$N$_2$O$_5$.0.1 H$_2$O (MW 456.37): C, 68.43; H, 7.55; N, 6.14; H$_2$, 0.39. Found: C, 68.13; H, 7.76; N, 6.09; H$_2$O, 0.22 (KF).

EXAMPLE 5

[1S-(1α,2α,3β,4α)]-2-[[3-[4-[(Pentylamino)carbonyl]-2-oxazolyl]-7-oxabicyclo[2.2.1]hept-2-yl]methyl]benzenepropanoic acid Aqueous 1N NaOH (5 mL) was added to a solution of Example 4 compound (0.912 g, 2 mmol) in THF (10 mL) and the reaction mixture was stirred under argon.

After 4.5 hours, the mixture was evaporated under vacuum to ~5 mL and diluted with 10 mL water. HCl (1 N, 2.8 mL) was added to the aqueous solution and its pH was adjusted to ~8.5 with a few drops of aqueous NaHCO$_3$. The solution was washed with EtOAc (15 mL), CH$_2$Cl$_2$ (10 mL) and EtOAc (15 mL). The aqueous layer was separated and acidified with 1 N HCl to pH 6.5. The product was extracted with EtOAc (150 mL) and CH$_2$Cl$_2$ (50 mL). Organic extracts were combined, dried (MgSO$_4$) and evaporated to give a white solid. The product was dried under vacuum overnight to furnish 0.808 g (yield 92%) of title acid, mp 157°-59°, $[\alpha]_D = +57.5°$ (c=1, CHCl$_3$).

Anal. Calc'd for C$_{25}$H$_{32}$N$_2$O$_5$ (MW 440.54): C, 68.16; H, 7.32; N, 6.36; H$_2$O, 0.0. Found: C, 67.99; H, 7.06; N, 6.33; H$_2$O, 0.0 (KF).

EXAMPLE 6

[1S-(1α,2α,3α,4α)]-2-[[3-[4-[(Diethylamino)carbon-yl]-2-oxazolyl]-7-oxabicyclo[2.2.1]hept-2-yl]methyl]benzenepropanoic acid methyl ester

A.

[1S-(1α,2α,3α,4α)]-2-[[3-[4-[(Diethylamino)carbonyl]-4,5-dihydro-2-oxazolyl]-7-oxabicyclo[2.2.1]hept-2-yl]methyl]benzenepropanoic acid, methyl ester Following the procedure as described in Example 1, Parts B and C, except substituting in Part B diethylamine for the Example 1, Part A(2) amine, the title oxazoline (dihydro) compound is prepared.

[1S-(1α,2α,3α,4α)]-2-[[3-[4-[(Diethylamino)carbonyl]-2-oxazolyl]-7-oxabicyclo[2.2.1]hept-2-yl]methyl]benzenepropanoic acid, methyl ester 1.1 g (2.5 mmol) of the Part A oxazoline was reacted (4 h) as described in Example 2, Part A to give, after purification by column chromatography on mL K-60 silica gel eluted with EtOAc/hexane (1:1), 0.87 g (80% yield) of the title oxazole as an oil: $[\alpha]_D = +23.8°$ (c=1.28, CHCl$_3$).

What is claimed is:

1. A method for preparing an oxazole of the structure

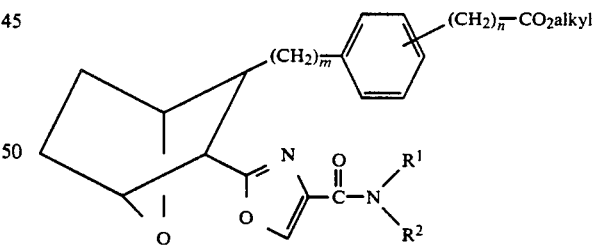

wherein m is 1, 2 or 3;

n is 0, 1, 2, 3 or 4;

R$^1$ is hydrogen, lower alkyl, aryl, aralkyl, cycloalkyl, cycloalkylalkyl, or an amide of the structure

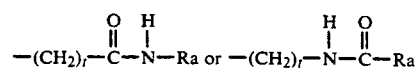

wherein t is 1 to 12 and Ra is lower alkyl, aryl, cycloalkyl or cycloalkylalkyl;

R$^2$ is hydrogen, lower alkyl, aryl, or aralkyl; or $R^1$ and $R^2$ together with the N to which they are linked form a 5- to 8-membered ring which has only the single N heteroatom, wherein the term aryl by itself or as part of another group refers to phenyl or naphthyl, or phenyl or naphthyl optionally substituted with 1 or 2 substituents which are lower alkyl, halogen, alkylsulfonyl and/or arylsulfonyl, which comprises providing an oxazoline of the structure

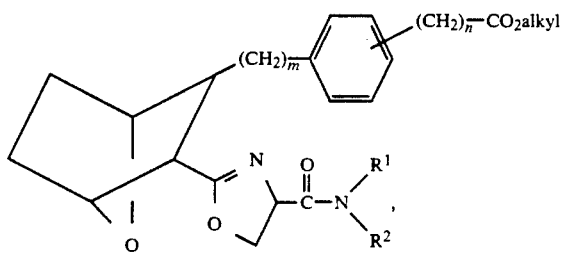

treating the oxazoline with an oxidizing agent which is cupric bromide or ferric bromide, a base which is 1,8-diazabicyclo[5.4.0]undec-7-ene (DBU) or 1,5-diazabicyclo[4.3.0]non-5-ene (DBN), and a non-hydride donor amine which does not have an αH or which will not easily lose an H at the α carbon under oxidation conditions and therefore will not undergo oxidation, to convert said oxazoline to the oxazole.

2. The method as defined in claim 1 wherein the non-hydride donor amine is hexamethylenetetraamine (HMTA), tert-butylamine, diazabicyclooctane (DABCO) or quinuclidine.

3. The method as defined in claim 1 wherein $R^1$ is hydrogen, $R^2$ is alkyl, m is 1 and n is 2.

4. The method as defined in claim 1 wherein $R^2$ is pentyl.

5. The method as in claim 3 wherein m is 1, n is 2, $R^1$ is H, $R^2$ is pentyl and $CO_2$alkyl is $CO_2CH_3$.

6. The method as defined in claim 5 wherein the oxidizing agent is cupric bromide, the base is DBU, and the non-hydride donor amine is hexamethylenetetraamine.

7. The method as defined in claim 1 wherein the oxazoline has the structure

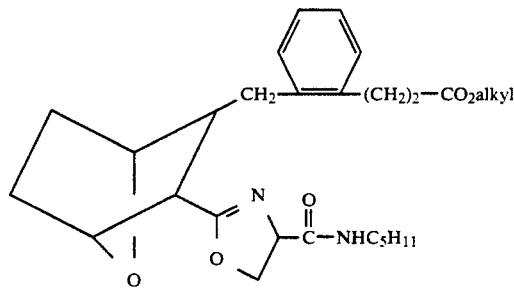

8. The method as defined in claim 1 wherein a single charge of cupric bromide, DBU and a non-hydride donor amine, which is hexamethylenetetraamine, is employed.

9. The method as defined in claim 1 wherein a double charge of cupric bromide, DBU and non-hydride donor amine, which is hexamethylenetetraamine, is employed.

10. The method as defined in claim 1 wherein the reaction is carried out in the presence of an inert organic solvent which is dichloromethane.

11. The method as defined in claim 1 wherein the reaction is carried out for a period within the range of from about 4 to about 24 hours.

12. The method as defined in claim 1 wherein the oxazole is recovered in substantially pure form.

13. The method as defined in claim 1 wherein the bromide is employed in a molar ratio to oxazoline within the range of from about 2.5:1 to about 5:1, the base is employed in a molar ratio to oxazoline of within the range of from about 2.5:1 to about 5:1, and the non-hydride donor amine base is employed in a molar ratio to oxazoline of within the range of from about 2.5:1 to about 5:1.

14. The method as defined in claim 11 wherein hexamethylenetetraamine is employed as the non-hydride donor amine and each of the cupric bromide, DBU and hexamethylenetetraamine will be employed in an amount to provide from about 3 to about 4 molar equivalents of each to each molar equivalent of oxazoline.

15. The method as defined in claim 14 wherein each of the cupric bromide, DBU and hexamethylenetetraamine are employed in an amount to provide about 4 molar equivalents of each to each molar equivalent of oxazoline.

16. The method as defined in claim 15 which is carried out for a period of from about 4 to about 6 hours.

17. The method as defined in claim 6 wherein each of the cupric bromide, DBU and non-hydride donor amine base will be divided into two charges and each of the first charges will be employed in amounts so as to provide a molar ratio of cupric bromide to oxazoline of within the range of from about 1.5:1 to about 2.5:1, a molar ratio of DBU to oxazoline of within the range of from about 1.5:1 to about 2.5:1, and a molar ratio of non-hydride donor amine to oxazoline of within the range of from about 1.5:1 to about 2.5:1.

18. The method as defined in claim 17 wherein the reaction of the oxazoline within the initial charge will be for a period within the range of from about 3 to about 10 hours, and thereafter, a second charge of each of the cupric bromide, DBU and nonhydride donor amine in amounts approximately the same as in the first charge will be added to the reaction mixture and the reaction will be continued for a period of within the range of from about 8 to about 15 hours.

19. A method for preparing an acid of the structure

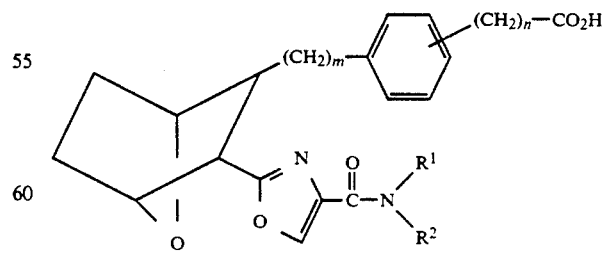

wherein
m is 1, 2 or 3;
n is 0, 1, 2, 3 or 4;
$R^1$ is hydrogen, lower alkyl, aryl, aralkyl, cycloalkyl, cycloalkylalkyl, or an amide of the structure

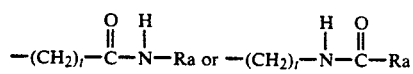

wherein t is 1 to 12 and Ra is lower alkyl, aryl, cycloalkyl or cycloalkylalkyl;

$R^2$ is hydrogen, lower alkyl, aryl, or aralkyl; or $R^1$ and $R^2$ together with the N to which they are linked form a 5- to 8-membered ring which has only the single N heteroatom, wherein the term aryl by itself or as part of another group refers to phenyl or naphthyl, or phenyl or naphthyl optionally substituted with 1 or 2 substituents which are lower alkyl, halogen, alkylsulfonyl and/or arylsulfonyl; which comprises providing an oxazoline of the structure

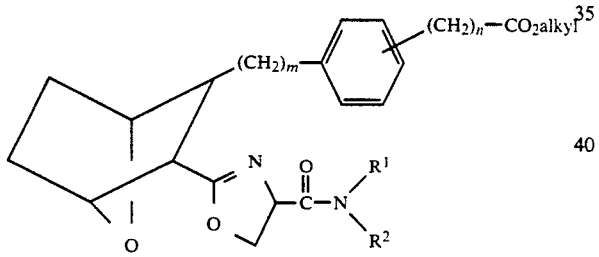

wherein m, n, $R^1$ and $R^2$ are as defined above, treating the oxazoline with an oxidizing agent which is cupric bromide or ferric bromide, a base which is 1,8-diazabicyclo[5.4.0]undec-7-ene (DBU) or 1,5-diazabicyclo[4.3.0]non-5-ene (DBN), and a non-hydride donor amine which does not have an αH or which will not easily lose an H at the α carbon under oxidation conditions and therefore will not undergo oxidation, to convert said oxazoline to an oxazole of the structure

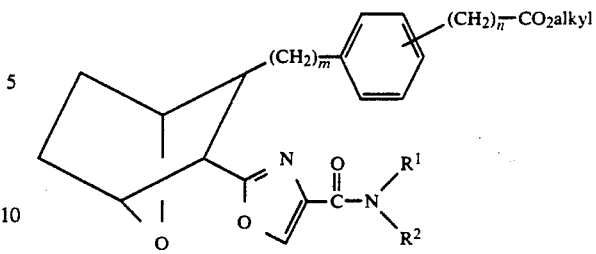

recovering the oxazole, and hydrolyzing the oxazole to the acid of the structure

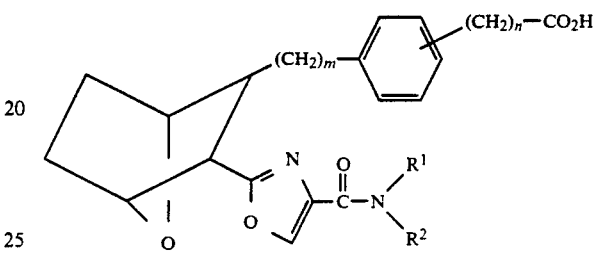

20. The method as defined in claim 19 wherein the non-hydride donor amine is hexamethylenetetraamine (HMTA).

21. The method as defined in claim 19 wherein $R^1$ is hydrogen, $R^2$ is pentyl, m is 1 and n is 2.

22. The method as defined in claim 19 wherein the oxazoline has the structure

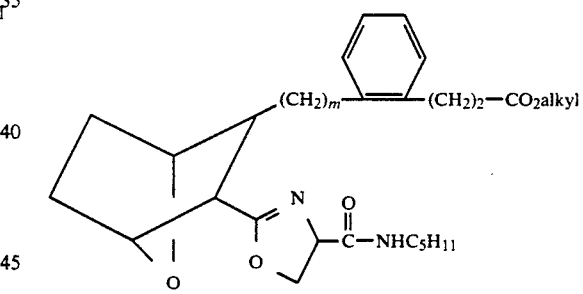

23. The method as defined in claim 19 wherein the oxidizing agent is cupric bromide, the base is DBU, and the non-hydride donor amine is HMTA.

24. The method as defined in claim 19 wherein a single charge of cupric bromide, DBU and non-hydride donor amine HMTA is employed.

25. The method as defined in claim 20 wherein a double charge of cupric bromide, DBU and non-hydride donor amine HMTA is employed.

26. The method as defined in claim 24 wherein each of the reactants of the single charge is employed in an amount to provide about 4 molar equivalents of each to each molar equivalent of oxazoline.

27. The method as defined in claim 26 wherein preparation of the oxazole ester is carried out for a period of from about 4 to about 6 hours.

* * * * *